United States Patent [19]

Adams

[11] Patent Number: 4,900,322
[45] Date of Patent: Feb. 13, 1990

[54] BLOOD COMPONENT POOLING VALVE AND KIT

[76] Inventor: James D. Adams, 4708 Creek Bend Dr., Austin, Tex. 78744

[21] Appl. No.: 254,440

[22] Filed: Oct. 5, 1988

Related U.S. Application Data

[62] Division of Ser. No. 910,367, Sep. 22, 1986, abandoned.

[51] Int. Cl.⁴ ............................................. A61M 5/00
[52] U.S. Cl. .................................... 604/410; 604/248
[58] Field of Search ......................................... 604/4–7, 604/32, 410, 248, 262, 403; 251/88; 206/438; 137/625.11, 625.47

[56] References Cited

U.S. PATENT DOCUMENTS

| | | | |
|---|---|---|---|
| 271,421 | 11/1983 | Fetterman | 604/248 |
| 913,321 | 2/1909 | Thomas . | |
| 2,434,723 | 1/1948 | Shook . | |
| 2,485,842 | 10/1949 | Pennington . | |
| 2,922,678 | 1/1960 | Schultz . | |
| 3,048,192 | 8/1962 | Murphy | 604/248 |
| 3,157,201 | 11/1964 | Littman | 604/32 |
| 3,344,785 | 10/1967 | Hamilton | 604/4 |
| 3,780,736 | 12/1973 | Chen . | |
| 3,834,372 | 9/1974 | Turney | 604/248 |
| 3,945,380 | 11/1976 | Dabney et al. | 604/410 |
| 3,957,082 | 5/1976 | Fuson et al. . | |
| 4,140,020 | 2/1979 | Cook . | |
| 4,199,079 | 8/1980 | Oloff et al. . | |
| 4,268,479 | 5/1981 | Webster . | |
| 4,351,799 | 12/1982 | Gross et al. . | |
| 4,378,560 | 2/1983 | Elsworth . | |
| 4,397,335 | 8/1983 | Doblar et al. . | |
| 4,608,996 | 9/1986 | Brown | 604/248 |

FOREIGN PATENT DOCUMENTS

| | | | |
|---|---|---|---|
| 807216 | 4/1951 | Fed. Rep. of Germany . | |
| 8300813 | 7/1983 | World Int. Prop. O. | 604/410 |

*Primary Examiner*—Stephen C. Pellegrino
*Attorney, Agent, or Firm*—Arnold, White & Durkee

[57] ABSTRACT

A valve adapted for pooling blood components comprising a valve housing and a valve plug, with channels through the valve plug. By rotating the valve plug, selected ports in the valve housing may be brought into communication so that fluids may flow between the ports in communication. To facilitate transfusions of blood components, the valve may be used to pool multiple units of blood components and to resuspend masses of component particles, enabling them to be drawn out of the blood component bag. The risk of infection is decreased, and a more efficient use of the contents of the blood component bags is obtained. A method for producing a blood component pooling device is also disclosed.

A containerized kit of the blood component pooling valve is provided which includes a rotary valve; a syringe adapted to be connected to the first port of the rotary valve; hoses, syringe fitting, hypodermic needle, and plastic bag needle to connect the other three ports to a capped vial of sterile saline solution, and a blood component pooling bag respectively; a sealed vial containing a sterile saline solution; a sterile blood component pooling bag; and a sterile sealed packet containing the kit elements.

23 Claims, 2 Drawing Sheets

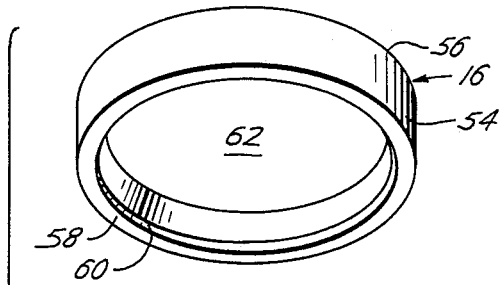
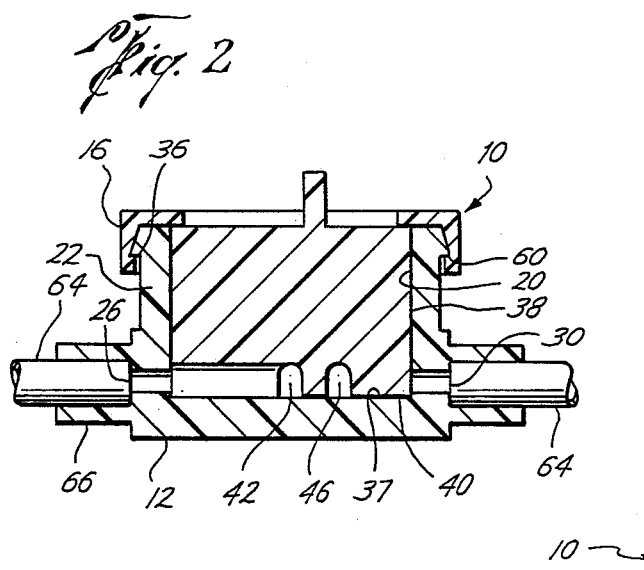
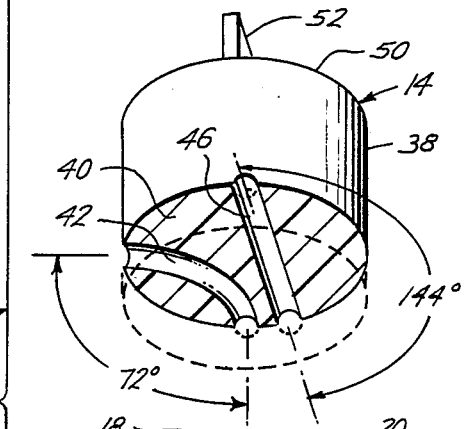
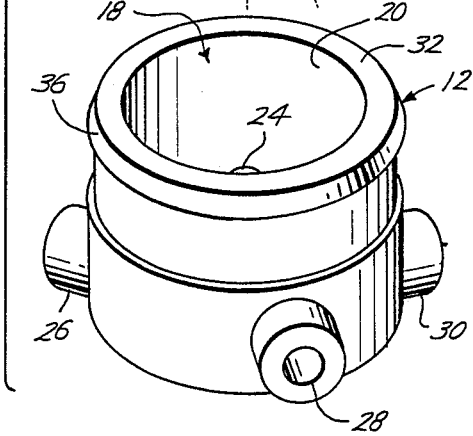
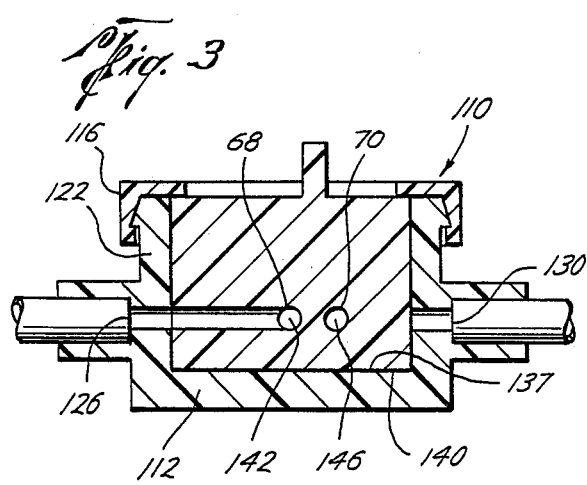
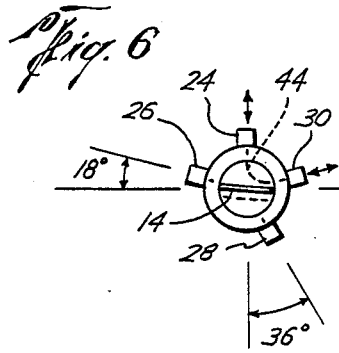
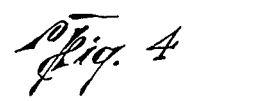
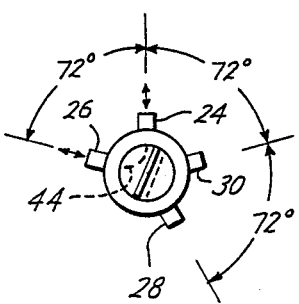
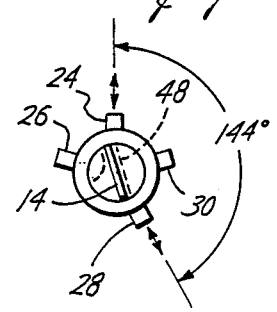

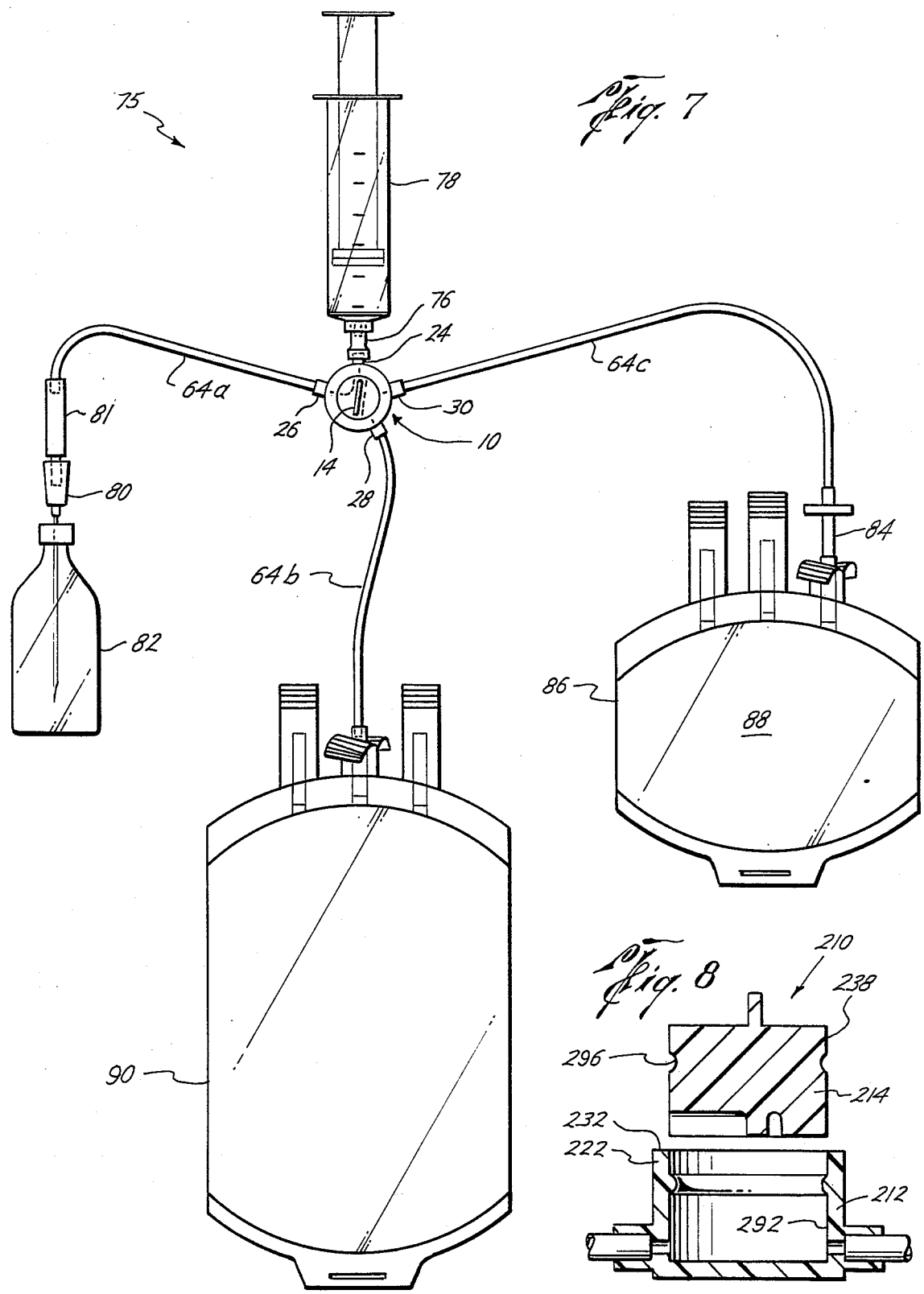

BLOOD COMPONENT POOLING VALVE AND KIT

This is a divisional of co-pending application, Ser. No. 910,367, filed Sept. 22, 1986.

FIELD OF THE INVENTION

This invention relates generally to a valve used in the transmission of fluids and, more particularly to a rotary valve used to facilitate the pooling of blood components.

BACKGROUND OF THE INVENTION

Transfusions of blood components, such as platelets and cryoprecipitates, are often required under current medical practice. For example, transfusions of platelets are sometimes required to stop serious bleeding in patients who experience a decrease in their number of platelets due to primary bone marrow failure and the resulting inadequate production of platelets. Transfusions of platelets are also sometimes required to control excessive bleeding in patients undergoing massive transfusions of blood. The excessive bleeding is related to the decrease in the number of platelets, which have a poor viability in stored blood, and platelet transfusions are sometimes necessary to control the excessive bleeding.

Under current medical techniques, when a patient requires transfusions of blood components, the medical personnel must attach several blood component bags to the patient in order to provide the necessary amount of components. Each blood component bag must be individually given to the patient. The existing method of transfusing blood components has several disadvantages.

Each time the contents of a blood component bag must be given to a patient, there is a risk of infection. A patient needing transfusions of blood components often requires several units of platelets, for example. Under existing medical techniques, each unit must be individually given to the patient, or a jury-rigged set up must be used, either way greatly increasing the risk of infection.

Also, since each blood component bag must be used individually, the nursing staff must spend a considerable amount of time tending to the patient when several units of blood components are to be transfused.

Blood components such as platelets and cryoprecipitates are very thick and tend to form sticky masses, which may clog the needles used in the transfusion unless the blood components are resuspended in a small amount of sterile saline solution. Under the existing transfusion methods, the blood component bags are individually connected to the patient: Saline solution cannot be easily added to the blood component bag, and the contents of the bag form a sticky mass that cannot be easily transfused into the patient. As a result, the patient often receives only 40–70% of the contents of a blood component bag.

Since, under the existing medical techniques, the entire content of the blood component bags cannot be easily transfused, the patient does not receive the full benefit of the units that his physician has ordered, nor does he receive the entire amount that he has paid for.

The following patents are, to the inventor's knowledge, the more generally pertinent references relating to the present invention.

West German Pat. No. 807,216, issued to Ulrich, describes a reusable metal valve used in the transfusion of blood from one person to another. A rotatable stopcock channels blood between a syringe port and ports leading to the donor, to the recipient, and to a saline solution source. By rotating the stopcock rather than the syringe, disturbance to the recipient and the donor is decreased.

This invention relates to a valve used in direct transfusions of blood between the donor and recipient. The valve is manufactured out of metal and is easily disassemblable into its component parts so that it may be thoroughly cleaned.

U.S. Pat. No. 4,397,335, issued to Doblar et al., describes a rotary valve used to measure pressures within the body and to administer medications and intravenous fluids, while minimizing the risk of contamination incurred when using multiple stopcocks.

U.S. Pat. No. 3,957,082, issued to Fuson et al., describes a stopcock that may be rotated to select fluids from any one of three inlet ports or a mixture of fluids from two adjacent inlet ports.

U.S. Pat. No. 3,780,736, issued to Chen, describes a four-way rotatable valve used in the irrigation of a patient's bladder following surgery. The valve may be rotated to bring a compressible bulb into communication with a urinary catheter or the source of the irrigating fluid. Also, the urinary catheter may be connected to a bedside urinary drainage bag without physically disconnecting any of the components.

A general object of the present invention is to provide a valve for use in blood component transfusions to make the transfusions safer and more efficient. Another object of the present invention is to provide a valve for use in blood component transfusions to enable the pooling of multiple units of the components before transfusion to the patient. Pooling the blood components prior to the transfusion has the effect that only one pooled blood component bag needs to be given to the patient. The risk of infection is thus decreased and the transfusion requires less attention by the nursing staff.

Still another object of the present invention is to provide a valve for use in blood component transfusions to enable the injection of sterile saline solution into the blood component bag. Particles in the blood component that may have formed a sticky mass may be resuspended in the saline solution so that they may be drawn out of the bag.

Yet another object of this invention is to make the valve in a disposable form by using such material as acrylic resins for its manufacture.

A further object of this invention is to provide a sterile kit to facilitate the pooling of blood components.

Other objects, uses and advantages of the present invention will be apparent to those skilled in the art upon examination of the accompanying description of the preferred embodiment in conjunction with the drawings.

SUMMARY OF THE INVENTION

The invention is a rotary valve relating generally to the transmission of fluids through different lines of communication, and relating specifically to the pooling of blood components.

The valve includes a valve housing having a bore extending partly therethrough. The bore is bounded by a surface of revolution, which forms the housing wall. Four ports are located on the housing wall opening into the bore. A valve plug is rotatably mounted in the valve housing and has two channels that extend through the plug. By rotating the valve plug within the valve housing, the channels bring the first port into exclusive communication with each of the other ports so that fluids may flow between the first port and the port with which it is in communication.

A blood component pooling device is produced by providing a blood component pooling valve, connecting a syringe to the first ports and connecting hoses to each of the other three ports. The hose connected to the second port is connected at its second end to a hypodermic needle, which may be inserted into a capped vial of sterile saline solution. The hose connected to the third port is connected at its second end to a plastic bag needle, which may be inserted into a plastic bag containing sterile blood components. The hose connected to the fourth port is connected at its second end to a blood component pooling bag.

In this invention, blood components may be pooled by providing a blood component pooling device and rotating the valve plug to bring the first port into successive communication with each of the other three ports. The blood component is first drawn out of the blood component bag into the syringe and then injected from the syringe into the blood component pooling bag. Next, saline solution is drawn into the syringe from the capped vial of saline solution and injected from the syringe into the blood component bag, thereby rinsing the blood component bag and resuspending the blood component particles. The rinsed contents of the blood component bag are then drawn into the syringe and injected from the syringe into the blood component pooling bag. Finally, the spent blood component bag is replaced with a new bag, and the procedure is repeated to pool contents of multiple blood component bags.

This invention facilitates the pooling of blood components such as platelets, cryoprecipitates, and other blood components that form sticky masses in the blood component bags making it difficult to draw the components out of the blood component bag.

In this invention, the pooling of blood components is facilitated by providing a containerized kit that furnishes: a rotary valve; a syringe adapted to be connected to the first port of the rotary valve; hoses, syringe fitting, hypodermic needle, and plastic bag needle to connect the other three ports to a capped vial of sterile saline solution, and a blood component pooling bag respectively; a sealed vial containing at least about 20 ml of sterile saline solution; a sterile blood component pooling bag; and a sterile sealed packet containing the kit elements.

BRIEF DESCRIPTION OF THE DRAWINGS

FIG. 1 is a perspective exploded view of a valve useful pooling blood components.

FIG. 2 is a side cross sectional view of the valve taken the centerline of the valve, in one preferred embodiment of the invention.

FIG. 3 is a side cross sectional view of the valve taken through the centerline of the valve, in another preferred embodiment of the invention.

FIG. 4 is a plan view of the valve showing the valve in a position so that the first and second ports are in exclusive communication.

FIG. 5 is a plan view of the valve showing the valve in a position so that the first and third ports are in exclusive communication.

FIG. 6 is a plan view of the valve showing the valve in a position so that the first and fourth ports are in exclusive communication.

FIG. 7 is an elevation view showing the invention in an operable condition with the blood component pooling kit in an assembled state with a blood component bag and kit components attached to the valve.

FIG. 8 is cross section exploded view showing another preferred embodiment of the invention wherein the retainer means comprises a ridge-groove retainer means.

DETAILED DESCRIPTION OF THE INVENTION

This invention relates to a rotary valve useful in pooling blood components. The valve includes a valve housing having a bore extending partly therethrough. The surface of revolution of the bore forms the valve housing side wall. Four ports are located in the side wall opening into the bore. A valve plug is rotatably mounted in the bore of the valve housing and has two channels that extend through the plug. By rotating the valve plug in the valve housing, the first port of the valve housing may be brought into exclusive communication with each of the other ports by means of the channels. Fluids may flow through the valve plug between only the first port and the port with which it is in communication.

The valve housing is generally cylindrical, with an annular side wall. The valve housing will typically be open at one end, and the valve plug has a handle extending through the opening. The upper surface of the valve plug may have directional indicators to designate the ports in communication.

The valve plug fits tightly within the valve housing so that fluids may flow only between the ports in communication through a channel.

The valve plug and valve housing are typically made of acrylic resins and are sterilizable for use with medical application. The valve assembly will generally not be disassemblable and will be of sufficiently low cost to be disposable after just one use.

In a preferred embodiment of the invention, the first port is a Luer-lock syringe fitting, and the other three ports are adapted to be connected to hoses. The second port is located at an angle of 72° around the circumference of the valve housing from the first port. The third port is located at an angle of 144° from the first port. The fourth port is located at an angle of 72° from the first port in the direction opposite the second port.

The channels in the valve plug are formed by grooves in the bottom surface of the valve plug. The first channel is adapted to connect the first port with either of the second or fourth ports. The channel is curved through the valve plug, the ends of the channel subtending an angle of 72°. The second channel is adapted to connect the first port with the third port. The channel is a chord of the circle defined by the circumference of the valve plug and the ends of the channel subtend an arc of 144° around the circumference.

In another preferred embodiment of the invention, the channels are tunnels extending through the body of the valve plug.

This invention is easily manufactured and produced and has great utility in the field of medicine. By using this invention, blood component transfusions become safer and more efficient. The blood components may be pooled before transfusion, decreasing the amount of time necessary for transfusions and decreasing the risk of infection to the patient. This invention enables saline solution to be injected into blood component bags during pooling, resuspending blood component particles and ensuring that the patient gets the full benefit of the treatment.

This invention provides a valve which is disposable, using a material such as acrylic resin in its manufacture. The valve is inexpensive, and sterilizing the disposable valve after use is not required.

This invention also provides a sterile kit for pooling blood components. All of the apparatus required to pool blood components is provided to the medical personnel in a sterile kit, making the pooling of blood components safe and economical.

Referring to the drawings in general and to FIG. 1 in particular, shown therein and designated generally by the general reference numeral 10 is a valve adapted for pooling blood components. The valve 10 includes a valve housing 12, a valve plug 14, and a retainer cap 16.

The valve housing 12 has a bore 18 extending partly therethrough that is bounded by a surface of revolution 20. The surface of revolution 20 is formed by the inner surface of the side wall 22 of the valve housing 12. The valve housing 12 has a firs port 24 opening into the bore 18 through the side wall 22. A second port 26, a third port 28, and a fourth port 30 similarly open into the bore 18 through the side wall 22.

The location of the ports relative to each other are shown in FIGS. 4, 5, and 6, wherein the angles between the ports may be seen. The second port 26 is located to form an angle of 72° with the first port 24. The third port 28 is located to form an angle of 144° with the first port 24. The fourth port 30 is located to form angle of 72° with the first port 24 opposite the second port 26. Other locations of ports may be possible and should be obvious to a person skilled in the art.

The first port 24 may comprise a Luer-lock syringe fitting adapted to connect a syringe. The second, third, and fourth ports (26, 28, 30) are adapted to be connected to hoses.

The valve housing 12 has a top surface 32, and the side wall 22 has an outer surface 34.

The outer surface 34 has a lip 36 near the top surface 32 extending radially outward from the valve housing 12. The lip 36, although present in this preferred embodiment, is not a necessary feature of the valve 10.

The valve housing 12 has a lower surface 37 which forms the limit of the extension of the bore 18 through the valve housing 12. The valve housing 12 is generally cylindrical and the side wall 22 is annular.

The valve plug 14 is rotatably mounted in the bore 18 of the valve housing 12. The valve plug 14 has an outer surface 38 which corresponds with the surface of revolution 20 of the bore 18 so that the valve plug 14 fits snugly within the valve housing 12 ensuring that fluids flow only through a channel between two ports in communication.

The valve plug 14 has a bottom surface 40 which corresponds with the lower surface 37 of the valve housing 12 so that the valve plug 14 fits snugly within the valve housing 12 ensuring that fluids flow only through a channel between two ports in communication.

In one embodiment the bottom surface 40 of the valve plug 14 has a first grooved 42 channel extending through the valve plug 14. The first channel 42 is curved, and the openings of the channel in the outer surface 38 subtend an angle of 72° to correspond with the angle between the first and second ports((24, 26) and the first and fourth ports (24, 30) in the valve housing side wall 22.

The bottom surface 40 of the valve plug 14 has a second grooved channel 46 through the valve plug 14. The second channel 46 is a chord of the circle defined by the outer surface 38 of the valve plug 14. The arc formed by this chord subtends an angle of 144° around the circumference of the circle, to correspond with the angle between the first and third ports (24, 28) in the valve housing side wall 22.

Other arrangements of the channels that correspond to the locations of the ports will be obvious to a person skilled in the art.

In FIG. 1, a more preferred embodiment is depicted by the phantom extensions of the bottom surface 40 of the valve plug 14. In this embodiment, the grooved channels 42, 46 are tunnels through the body of the valve plug 14 which provide communication between the various ports. To accommodate the grooved channels 42, 46 of this embodiment (referred to as 142, 146, respectively, in FIG. 3), the bottom surface 40 (140) of the valve plug 14 (114) and the lower surface 37 (137) of the valve housing 12 (112) are recessed relative to the ports 24, 26, 28 30.

The valve plug 14 has a top surface 50 and has a handle 52 protruding from the top surface 50. The top surface 50 may have directional indicators (not shown) that indicate the ports in communication.

The retainer cap 16 is generally annular shaped and has a side wall 54 and a top surface 56, which extends radially inward a limited distance toward the center of the annulus formed by the side wall 54.

The retainer cap 16 has a bottom surface 58 and has a lip 60 at the bottom surface which extends radially inward a short distance toward the center of the annulus from the side wall 54. The lip 60 of the retainer cap engages with the lip 36 of the valve housing side wall 22 when the valve 10 is assembled. The retainer cap 16, although present in this preferred embodiment, is optional when a single disposable valve 10 is used.

The top of the retainer cap 16 has a hole 62 formed by the limited extension of the top surface 56 toward the center of the annulus, and has a diameter less than the greatest diameter of the valve plug 14, so that when the valve 10 is assembled, the valve plug 14 is held within the valve housing 12 by the retainer cap 16.

The valve housing 12, valve plug 14, and retainer cap 16 are ideally made of acrylic resins, although other materials for its manufacture will be obvious to one skilled in the art. The valve elements are sterilizable for use in medical applications. The elements are sufficiently inexpensive that the valve 10 is disposable after just one use in order to facilitate its application as part of a kit and to prevent having to sterilize the valve before each use.

FIG. 2 shows the valve 10 in an assembled state, with the valve plug 14 seated within the valve housing 12 and held in place by the retainer cap 16. The lip 60 of the retainer cap 16 is engaged with the lip 36 of the valve housing side wall 22.

The bottom surface 40 of the valve plug 14 engages with the lower surface 37 of the valve housing 12 so that fluids may flow between ports in the valve housing only through the grooved channels 40, 46 in the valve plug 14.

The first port 28 (not shown in FIG. 2) is a syringe fitting, so that it is adapted to be connected to a syringe. The first port may be a Luer-lock syringe fitting, although other syringe fittings may be used.

The second port 26, third port 24 (not shown in FIG. 3) and fourth port 30 are adapted to connect hoses 64. As an example, the second port 26 has an annular hose housing 66 extending from the valve housing 12 at the port. The port 26 has a diameter equal to the inside diameter of the hose 64 to minimize the turbulence in the fluid flowing from the hose to the port. The hose housing 66 has an inside diameter equal to the outside diameter of the hose 64, so that the hose fits snugly within the housing. The second port 26 is located at the bottom of the side wall 22 at the lower surface 37 of the valve housing 12 to correspond with the grooved channels 42, 46 in the bottom surface 40 of the valve plug 14.

The third port 24 and fourth port 30 are of a similar construction to the second port 26.

With reference to FIG. 3 of the drawings, reference numeral 110 refers generally to an alternative and more preferred embodiment of the valve adapted for pooling blood components in accordance with this invention.

The valve 110 corresponds substantially with the valve 10, and corresponding parts are therefore indicated by corresponding reference numerals except that the prefix "1" is used before each numeral.

FIG. 3 shows the valve 110 in an assembled state with the valve plug 114 seated within the valve housing 112 and held in place by the retainer cap 116.

The grooved channels 142, 146 are formed by holes 68, 70 extending through the valve plug 114. The ports (e.g. 126, 130) are located in the valve housing side wall 122 at a distance above the valve housing lower surface 137 to correspond with the height of the grooved channels 146, above that surface.

The embodiment shown in FIG. 3 is the more preferred embodiment because there is a decreased likelihood of leakage through the valve plug. In this invention, the valve is adapted to transmit fluids only between ports in communication through a channel, and possibility of leakage should be small. Since leakage occurs where two surface contact each other, these areas of contact should be kept to a minimum. The embodiment shown in FIG. 3 is the more preferred embodiment since there is a possibility of leakage only in the immediate vicinity of the ports. In the embodiment shown in FIG. 2, there is a possibility of leakage along the entire length of the channels where the valve plug contacts the valve housing.

In another alternative embodiment of the invention, the retainer cap is not used. The means for rotatably retaining the valve plug in valve housing bore is provided by a rounded annular groove in the outer surface of the valve plug and a corresponding rounded annular ridge on he inner surface of the valve housing side wall. When the valve is assembled, the groove and the ridge snappingly engage so that the valve plug is retained in the valve housing in a non-disassemblable condition. With this embodiment, once manufactured and assembled, the valve is not intended to be disassembled.

This embodiment is illustrated in FIG. 8 of the drawings. Reference numeral 210 refers generally to this embodiment of a valve adapted for pooling blood components in accordance with this invention. The figure shows the valve before it is finally assembled.

The valve 210 corresponds substantially with the valve 10, and corresponding parts are therefore indicated by corresponding reference numerals except that the prefix "2" is used before each numeral.

FIG. 8 shows the valve plug 214 and valve housing 212 before they have been finally assembled.

The valve housing side wall 222 has an inner surface 292 and has a rounded annular ridge 294 extending radially inward from the inner surface 292, and located proximate to the top surface 232 of the valve housing 212.

The valve plug 214 has a rounded annular groove 296 in the outer surface 238 of the valve plug 214 and located to correspond with the ridge 294 on the valve housing side wall 212.

When the valve is assembled, the ridge 294 of the valve housing 212 snappingly engages with the groove 296 in the valve plug 214. Once assembled, the valve is not intended to be disassembled. Providing a ridge-groove retaining means rather than a retainer cap is more economical since fewer parts must be produced and assembled. The ridge-groove means also provides more assurance that the valve will not be disassembled.

Referring now to FIG. 7, reference numeral 75 refers generally to a blood component pooling device.

The blood component pooling device 75 is produced by first providing a valve 10 adapted for pooling blood components. The valve 10 has a first port 24 with a syringe fitting 76, and a second port 26, a third port 28, and a fourth port 30, adapted to connect hoses. The syringe fitting 76 may be a Luer-lock syringe fitting, although other fittings may be commercially available.

A syringe 78 is then connected to the syringe fitting 76 at the first port 24. The syringe 78 typically has at least a 20 ml capacity and is ideally a 60 ml syringe, although other sizes of syringes may be used. A 35 cc syringe may be obtained from Monoject Scientific (Cat. No. B2965-35), and a 50 cc syringe may be obtained from American Pharmaseal (Cat. No. 39520-50).

Hoses 64a, 64b, 64c, are then connected to the second port 26, third port 28, and fourth port 30 respectively. The hoses 64a, 64b, 64c are ideally between about 20 cm and 50 cm in length and made of a polymerized vinyl compound. Tygon tubing hoses are well suited for this purpose and may be obtained from American Scientific Products, 1430 Waukegan Rd., McGaw Park, Ill., 60085. The hoses will typically have an outer diameter of 5/32 inch and an inner diameter of 3/32 inch, with a wall thickness of 1/32 inch. The model Tygon S50-H1 (Cat. No. T6034-3T) is ideal.

A hypodermic needle 80 is connected to the second end of the first hose 64a by means of a second syringe fitting 81. The hypodermic needle is insertable into a capped vial of sterile saline solution 82. The hypodermic needle is preferably 20 gauge and may be obtained from Monoject Scientific, St. Louis, Mo., 63103 (H.R.I. No. 8881-216033).

The second hose 64b is connectable at its second end to a blood component pooling bag 90.

A plastic bag needle 84 is connected to the second end of the third hose 64c. The plastic bag needle is insertable into a plastic blood component bag 86 containing sterile blood components 88, such as platelets or cryoprecipitates. The plastic bag needle may be obtained from McGaw Laboratories, Inc., Sabana Grande, Puerto Rico, 00747 (Cat No. V1420-15).

This invention includes a kit which facilitates the pooling of blood components. The kit provides, in a sterile sealed packet (not shown), a blood component pooling device 75 and additional items to facilitate the pooling of blood components.

The kit includes a valve 10 adapted for pooling blood components. The valve 10 provided in the kit is sterilized for use in medical applications. The valve 10 is not disassemblable and is made out of a sufficiently inexpensive material, such as acrylic resins, so that the valve is economically disposable.

The kit also includes three hoses 64a, 64b, 64c adapted to connect to the second port 26, the third port 28, and the fourth port 30, respectively, of the valve 10. The hoses are between about 20 cm and 50 cm in length and are made of a polymerized vinyl compound.

The first port 24 has a syringe fitting 76, which may be a Luer-lock syringe fitting. Also included in the kit is a syringe 78, adapted to connect with the syringe fitting 76. The syringe 78 has a capacity of at least 20 ml, and preferably has a capacity of about 60 ml.

The kit includes a sealed vial of sterile saline solution 82 containing at least 20 ml and ideally 60 ml of sterile saline solution. Bacteriostatic saline solution for injection is manufactured by Elkins-Sinn, Inc., Cherry Hill, N.J., 08034. The kit also provides a hypodermic needle 80 insertable into the sealed vial of sterile saline solution 82, and a second syringe fitting 81 adapted to join an end of the first hose 64a with the hypodermic needle 80.

A plastic bag needle 84 is provided by the kit to connect an end of the third hose 64c with a blood component bag 86 and the sterile blood components 88 contained therein.

Also included in the kit is a sterile blood component pooling bag 90 adapted to connect with an end of the second hose 64b. The blood component pooling bag 90 is large enough to contain the contents of two blood component bags and about 20 ml of saline solution. The pooling bag should be at least a 300 ml plastic bag (No. 4R2014) and may be a 600 ml plastic bag (No. 4R2023).

Directional indicators (not shown) may be provided on the upper surface of the valve plug 14 of the valve 10 to indicate to medical personnel the ports in communication.

All of the components of the kit are provided in a sterilized and aseptic condition in a sterile sealed packet (not shown). All of the components are disposable and inexpensive to prevent the necessity of re-sterilizing the equipment before another medical application. By providing an inexpensive, disposable, sterilized kit, medical personnel are freed from the burden of sterilizing the equipment before pooling blood components. Patients as well are assured of using a sterile kit.

Multiple blood components units may be more quickly and efficiently administered to patients if they are first pooled and then transfused as one unit. The present invention includes a method of pooling blood components.

Referring now to FIGS. 4 through 7, blood components may be pooled by first providing a valve 10 adapted for pooling blood components. The valve 10 includes generally a valve housing with four ports, and a valve plug with two channels, as heretofore described.

A syringe 78 with a capacity of about 60 ml, is then connected to the first port 24, and three hoses 64a, 64b, 64c are connected respectively to each of the other three ports 26, 28, 30. The hoses are between about 20 cm and 60 cm in length are ideally made out of a polymerized vinyl compound.

The second end of the first hose 64a is connected to a syringe fitting 81, which is in turn connected to a hypodermic needle 80. The hypodermic needle 80 is inserted into a capped vial of sterile saline solution 82.

The second end of the second hose 64b is connected to a blood component pooling bag.

The second end of the third hose 64c is connected to a plastic bag needle 84 for insertion into the blood component bag 86.

Blood components in separate blood component bags may be pooled according to the following steps shown most clearly in connection with FIGS. 4, 5, 6, and 7:

1. Connect a blood component bag 86 containing sterile blood components 88 to the plastic bag needle 84.

2. Rotate the valve plug 14 of the valve 10 to the position shown in FIG. 6. In this position, the first channel 44, which subtends an arc of 72° around the circumference of the valve plug will bring the first port 24 and the fourth port 30, which are at an angle of 72° to each other, into communication.

3. Draw the contents 88 of the blood component bag 86 through the plastic bag needle 84, the third hose 64c, the fourth port 30, and the valve 10 into the syringe 78.

4. Rotate the valve plug 14 of the valve 10 to the position shown in FIG. 5. In this position, the second channel 48 brings the first port 24 and the third port 28 into communication.

5. Inject the blood components contained in the syringe 78 through the valve 10, the third port 28, and the second hose 64b and into the blood component pooling bag 90.

6. Rotate the valve plug 14 of the valve 10 to the position shown in FIG. 4. In this position, the first channel 44, which subtends an arc of 72° around the circumference of the valve plug, brings the first port 24 and the second port 26, which are at an angle of 72° to each other, into communication.

7. Draw about 20 ml of saline solution from the capped vial of saline solution 82, through the hypodermic needle 80, the syringe fitting 81, the first hose 64a, the second port 26, and the valve 10 into the syringe 78.

8. Rotate the valve plug 14 to the position shown in FIG. 6, bringing the first port 24 into communication with the fourth port 30 through the first channel 44.

9. Inject the saline solution contained in the syringe 78 into the blood component bag 86.

10. Rinse the blood component bag 86 with the saline solution to resuspend any massed particles of the blood components.

11. Draw the saline solution-component particle suspension contained in the blood component bag 86 into the syringe 78.

12. Rotate the valve plug 14 to the position shown in FIG. 5, bringing the first port 24 into the communication with the third port 28 through the second channel 48.

13. Inject the saline solution-component particle suspension contained in the syringe 78 into the blood component pooling bag.

If another unit of blood components is to be pooled, the spent blood component bag 86 is removed from the plastic bag needle 84 and the plastic needle 84 is inserted into another blood component bag containing fresh blood components. Steps 1–13 are repeated until the necessary number of blood component units is pooled.

If the required units of blood components have been pooled, the blood component pooling bag 90 is removed from the second hose 64b and sealed the blood component units are pooled and are; ready to be transfused to the patient. The assembled blood component pooling device can be disposed.

This method of pooling blood components may be used with any kind of components, but is especially useful in pooling components such as platelets and cryoprecipitates. The components are very thick and form sticky masses in the blood component pooling bag which cannot be drawn out by a syringe. By rinsing the blood component bag with sterile saline solution, the massed particles of blood components may be resuspended, allowing their withdrawal into a syringe Changes may be made in the construction, operation and arrangement of the various parts, elements, steps and procedures described herein without departing from the concept and scope of the invention as defined in the following claims.

What is claimed is:

1. A method of producing a blood component pooling device for pooling platelets or cryoprecipitates, the method comprising:
   (a) providing a valve comprising: a valve housing having a bore extending partly therethrough that is bounded by a surface of revolution that is defined by a side wall of the housing, said housing having four ports opening into its bore through the side wall of the housing; and a valve plug rotatably mounted in the bore of said housing, and having two non-intersecting channels extending therethrough, said channels being arranged to that by rotation of the valve plug a first port, with a syringe fitting, may be brought into exclusive communication with each of the other ports so that fluids may flow only between the first port and the port in communication therewith;
   (b) connecting a syringe to the first port;
   (c) connecting a first hose to a second port, said first hose being connected at its second end to a terminal hypodermic needle;
   (d) connecting a second hose to a third port said second hose being connectable at its second end to a blood component pooling bag; and
   (e) connecting a third hose to a fourth port, said third hose being connected at its second end to a plastic bag needle insertable into a blood component bag containing platelets or cryoprecipitates.

2. The method of claim 1 wherein the syringe is a 60 ml syringe.

3. The method of claim 1 wherein each hose comprises a polymerized vinyl compound.

4. The method of claim 1 wherein each hose is between about 20 cm and about 50 cm in length.

5. A method of pooling blood components, the method comprising steps to:
   (a) provide a blood component pooling device, as describe in any of claims 1, 2, 3 or 4;
   (b) rotate the valve plug to bring the first port into successive communication with each of the other three ports to thereby withdraw cryoprecipitates from a blood component bag and inject the cryoprecipitates into a blood component pooling bag;
   (c) withdraw saline solution from a saline solution source and inject the saline solution into the blood component bag;
   (d) withdraw the saline solution from the blood component bag and inject the saline solution into the blood component pooling bag; and
   (e) replace the blood component bag with a full blood component bag.

6. A method of pooling blood components, the method comprising steps to:
   (a) provide a blood component pooling device, as described in any one of claims 1, 2, 3 or 4;
   (b) rotate the valve plug to bring the first port into successive communication with each of the other three ports to thereby withdraw platelets from a blood component bag and inject the platelets into a blood component pooling bag;
   (c) withdraw saline solution from a saline solution source and inject the saline solution into the blood component bag;
   (d) withdraw the saline solution from the blood component bag and inject the saline solution into the blood component pooling bag; and
   (e) replace the blood component bag with a full blood component bag.

7. The method of claim 6 wherein the syringe is a 60 ml syringe.

8. The method of claim 6 wherein each hose comprises a polymerized vinyl compound.

9. The method of claim 6 wherein each hose is between about 20 cm and 50 cm in length.

10. A method of pooling blood components comprising the steps of:
    (a) providing a valve adapted for pooling blood components described in the method of claim 1;
    (b) connecting a syringe to the first port;
    (c) connecting a first hose to a second port, said first hose being connected at its second end to a terminal hypodermic needle;
    (d) connecting a second hose to a third port, said second hose being connectable at its second end to a blood component pooling bag;
    (e) connecting a third hose to a fourth port, said third hose being connected at its second end to a plastic bag needle;
    (f) inserting the hypodermic needle into a capped vial of sterile saline solution;
    (g) inserting the plastic bag needle into a blood component bag containing platelets or cryoprecipitates;
    (h) connecting the second end of the second hose to a blood component pooling bag;
    (i) rotating the valve plug so that a channel brings the first port into communication with the fourth port;
    (j) drawing the contents of the blood component bag into the syringe;
    (k) rotating the valve plug so that a channel brings the first port into communication with the third port;
    (l) injecting the contents of the syringe into the blood component pooling bag;
    (m) rotating the valve plug so that a channel brings the first port into communication with the second port;
    (n) drawing about 20 ml of saline solution into the syringe;
    (o) rotating the valve plug in the valve housing so that a channel brings the first port into communication with the fourth port;
    (p) injecting the contents of the syringe into the blood component bag;
    (q) rinsing the blood component bag with the saline solution;
    (r) drawing the contents of the blood component bag into the syringe;
    (s) rotating the valve plug so that a channel brings the first port into communication with the third port;

(t) injecting the contents of the syringe into the blood component pooling bag;

(u) replacing the blood component bag with a full blood component bag; and (v) repeating steps (i) through (u).

11. A kit for facilitating the pooling of the contents of blood component bags comprising:

(a) a valve including: a valve housing having a bore extending partly therethrough that is bounded by a surface of revolution that is defined by the side wall of the housing, said housing having four ports opening into its bore through the side wall of the housing and a valve plug rotatably mounted in said housing; and having two non-intersecting channels extending therethrough, said channels being arranged so that by rotation of the valve plug a first port with a syringe fitting, may be brought into exclusive communication with each of the other ports so that fluids may flow only between the first port and the port in communication therewith;

(b) a syringe with a capacity of at least about 20 ml and connectable to the first port of the valve;

(c) a first, second, and third hose adapted respectively to connect to a second, third, and fourth port of the valve;

(d) a second syringe fitting adapted to connect an end of the first hose to a hypodermic needle;

(e) a hypodermic needle connectable to said second syringe fitting and adapted to withdraw fluid from a sealed vial of sterile solution;

(f) a sealed vial containing at least about 20 ml of sterile saline solution;

(g) a plastic bag needle adapted to connect an end of the third hose and contents of a blood component bag;

(h) a sterile blood component pooling bag adapted to be connected to the second hose and to contain at least the contents of two standard blood component bags and about 20 ml of sterile saline solution; and (i) a sealed packet containing the items described in steps (a) to (h).

12. The kit of claim 11 wherein the valve housing and valve plug are acrylic resins.

13. The kit of claim 11 wherein the syringe fitting is a Luer-lock syringe fitting.

14. The kit of claim 11 wherein the syringe is a 60 ml syringe.

15. The kit of claim 11 wherein each hose comprises a polymerized vinyl compound.

16. The kit of claim 11 wherein each hose is between about 20 cm and about 50 cm in length.

17. The kit of claim 11 wherein the sealed vial contains about 60 ml of sterile saline solution.

18. The kit of claim 11 wherein the valve plug has an upper surface and the upper surface has directional indicators designating the ports in communication.

19. The kit of claim 11 wherein the kit is sterilized.

20. The kit of claim 11 wherein the kit is disposable.

21. The kit of claim 11 wherein the sealed packet is sterile.

22. The kit of claim 11 also comprising a blood component bag containing concentrated platelets.

23. The kit of claim 11 also comprising a blood component bag containing cryoprecipitates.

* * * * *